United States Patent
Yaoka et al.

(10) Patent No.: US 11,976,453 B2
(45) Date of Patent: May 7, 2024

(54) SANITARY WASHING DEVICE

(71) Applicant: TOTO LTD., Kitakyushu (JP)

(72) Inventors: Toshinari Yaoka, Kitakyushu (JP);
Kazuma Baba, Kitakyushu (JP);
Satoru Matsumoto, Kitakyushu (JP);
Keisuke Tashiro, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 689 days.

(21) Appl. No.: 17/098,728

(22) Filed: Nov. 16, 2020

(65) Prior Publication Data

US 2021/0164211 A1 Jun. 3, 2021

(30) Foreign Application Priority Data

Nov. 29, 2019 (JP) .................. 2019-217489

(51) Int. Cl.
*E03D 9/08* (2006.01)
*A61L 2/08* (2006.01)
*A61L 2/18* (2006.01)

(52) U.S. Cl.
CPC ............... *E03D 9/08* (2013.01); *A61L 2/08* (2013.01); *A61L 2/18* (2013.01); *A61L 2202/11* (2013.01); *A61L 2202/17* (2013.01)

(58) Field of Classification Search
CPC ..... E03D 9/08; A61L 2/08; A61L 2/18; A61L 2202/11; A61L 2202/17; A61L 2/183; A61L 2/22; A61L 2202/14; A61L 2202/15; A61L 2/035; A61L 2/084; A61L 2/10; A61L 2202/122

USPC ..... 4/448, 447, 420.4, 443, 446, 422, 420.5, 4/445, 444

See application file for complete search history.

(56) References Cited

U.S. PATENT DOCUMENTS

| | | | |
|---|---|---|---|
| 10,851,533 B2* | 12/2020 | Yaoka | A61L 2/084 |
| 10,907,334 B2* | 2/2021 | Yaoka | A47K 7/08 |
| 11,479,958 B2* | 10/2022 | Baba | A61L 2/18 |
| 2013/0185861 A1 | 7/2013 | Matsumoto et al. | |
| 2021/0164212 A1* | 6/2021 | Baba | A61L 2/084 |

FOREIGN PATENT DOCUMENTS

| CN | 103041413 A | 4/2013 |
|---|---|---|
| CN | 103088891 A | 5/2013 |
| CN | 209285423 U | 8/2019 |

(Continued)

*Primary Examiner* — Lori L Baker
(74) *Attorney, Agent, or Firm* — PEARNE & GORDON LLP

(57) ABSTRACT

A sanitary washing device includes a private part washing nozzle, a casing, a sterilizing water generator, and an illuminator. The private part washing nozzle discharges water toward a private part of a user in a state of the private part washing nozzle is advanced into a toilet. The casing includes a nozzle storage part configured to store an entirety of the private part washing nozzle in a state of the private part washing nozzle is retracted. The sterilizing water generator generates sterilizing water supplied to the private part washing nozzle and the nozzle storage part. The illuminator irradiates sterilizing light into the nozzle storage part. The sterilizing light has a sterilizing action. The illuminator irradiates the sterilizing light toward a residual water occurrence portion at which the sterilizing water supplied into the nozzle storage part remains.

10 Claims, 12 Drawing Sheets

(56) References Cited

FOREIGN PATENT DOCUMENTS

| | | | |
|---|---|---|---|
| JP | 2006-274641 | A | 10/2006 |
| JP | 2010-084335 | A | 4/2010 |
| JP | 2010-189849 | A | 9/2010 |
| JP | 2013-083141 | A | 5/2013 |
| KR | 10-2013-0038661 | A | 4/2013 |
| TW | 201207201 | A1 | 2/2012 |

* cited by examiner

SANITARY WASHING DEVICE

CROSS-REFERENCE TO RELATED APPLICATIONS

This application is based upon and claims the benefit of priority from Japanese Patent Application No. 2019-217489, filed on Nov. 29, 2019; the entire contents of which are incorporated herein by reference.

FIELD

Embodiments described herein relate generally to a sanitary washing device.

BACKGROUND

JP-A 2013-83141 (Kokai) discusses a sanitary washing device including a private part washing nozzle. To remove dirt adhered to the private part washing nozzle in the sanitary washing device, sterilizing water (bacteria removing water) is squirted toward the private part washing nozzle, and sterilizing light (ultraviolet light) that has a sterilizing action is irradiated toward the private part washing nozzle.

The sterilizing water that is squirted toward the private part washing nozzle spreads in a nozzle storage part in which the private part washing nozzle is stored. The concentration of the sterilizing component of the squirted sterilizing water decreases over time. There is a risk that bacteria and/or mold may easily occur due to the effects of moisture at locations where the sterilizing water having a reduced sterilizing effect remains.

Accordingly, when sterilizing water remains in the nozzle storage part, it is desirable to suppress the occurrence of bacteria and/or mold by irradiating sterilizing light also toward such locations.

However, because the sterilizing light basically travels straight, it is difficult to irradiate the sterilizing light toward a wide area inside the nozzle storage part. Because it is necessary to provide many light sources and/or reflective materials to irradiate the sterilizing light toward a wide area inside the nozzle storage part, there is a risk that the casing may become large or the cost may increase.

SUMMARY

According to the embodiment, a sanitary washing device includes a private part washing nozzle, a casing, a sterilizing water generator, and an illuminator. The private part washing nozzle discharges water toward a private part of a user in a state of the private part washing nozzle is advanced into a toilet. The casing includes a nozzle storage part configured to store an entirety of the private part washing nozzle in a state of the private part washing nozzle is retracted. The sterilizing water generator generates sterilizing water supplied to the private part washing nozzle and the nozzle storage part. The illuminator irradiates sterilizing light into the nozzle storage part. The sterilizing light has a sterilizing action. The illuminator irradiates the sterilizing light toward a residual water occurrence portion at which the sterilizing water supplied into the nozzle storage part remains.

DETAILED DESCRIPTION

Figure 1:
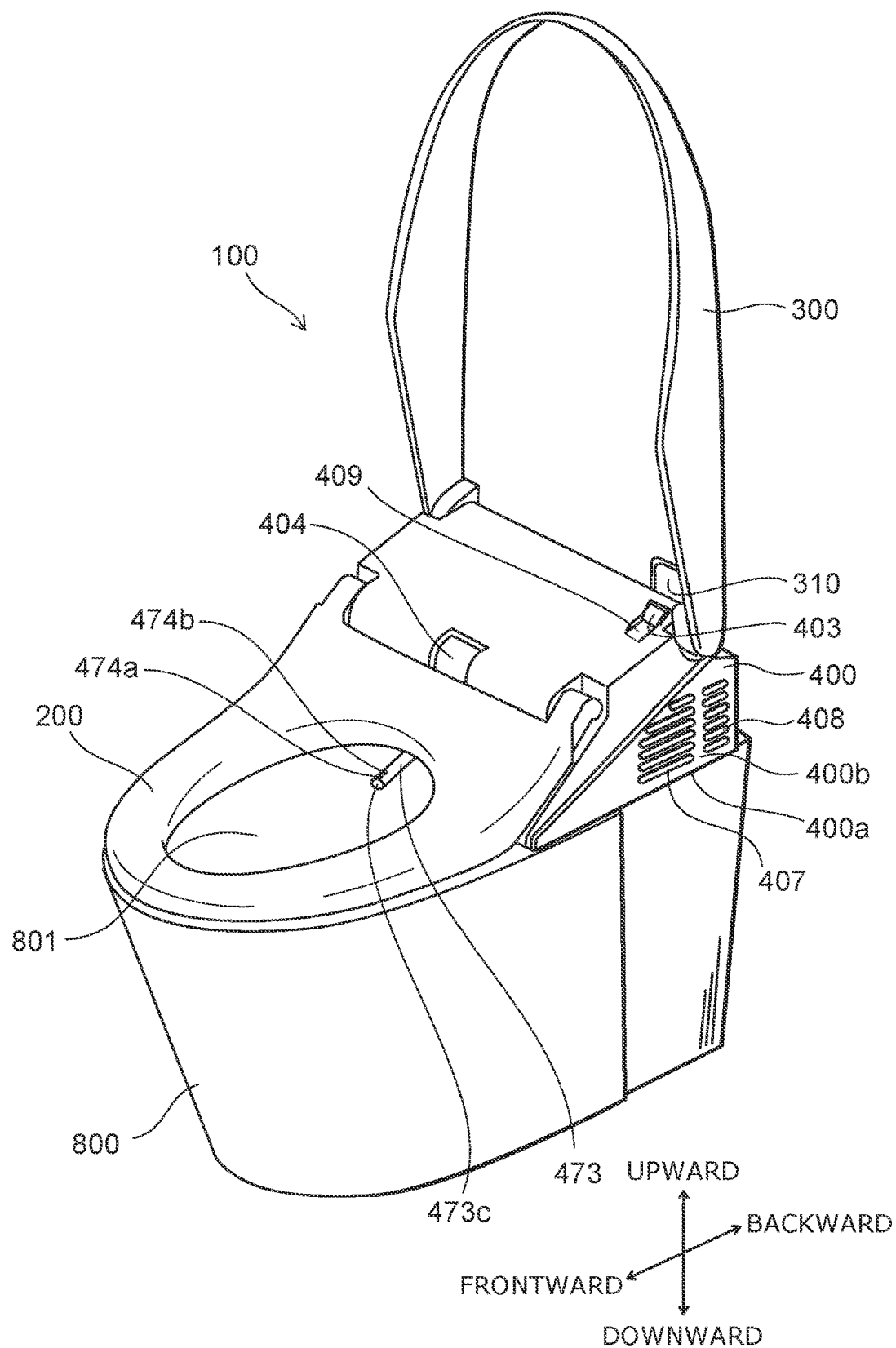
FIG. 1 is a perspective view illustrating a toilet device including a sanitary washing device according to the embodiment.

According to one embodiment, a sanitary washing device including a private part washing nozzle discharging water toward a private part of a user in a state of the private part washing nozzle being advanced into a toilet, a casing including a nozzle storage part configured to store an entirety of the private part washing nozzle in a state of the private part washing nozzle being retracted, a sterilizing water generator generating sterilizing water supplied to the private part washing nozzle and the nozzle storage part, and an illuminator irradiating sterilizing light into the nozzle storage part, such that the sterilizing light has a sterilizing action, and the illuminator irradiates the sterilizing light toward a residual water occurrence portion at which the sterilizing water supplied into the nozzle storage part remains.

According to the sanitary washing device, washing and sterilizing the private part washing nozzle and the nozzle storage part can be performed by the sterilizing water. In other words, the sterilizing water can sterilize a wide area of the private part washing nozzle and the interior of the nozzle storage part. The illuminator sterilizes by irradiating sterilizing light toward the residual water occurrence portion at which the sterilizing water remains inside the nozzle storage part. In other words, the illuminator irradiates the sterilizing light toward the residual water occurrence portion at which bacteria and/or mold easily occurs. Accordingly, even without providing multiple light sources, reflective materials, etc., the clean state of the private part washing nozzle and the nozzle storage part can be efficiently maintained using the sterilizing water and the sterilizing light, and the enlargement of the casing can be suppressed.

Embodiments of the invention will now be described with reference to the drawings. Similar components in the drawings are marked with the same reference numerals, and a detailed description is omitted as appropriate.

FIG. 1 is a perspective view illustrating a toilet device including a sanitary washing device according to the embodiment.

As illustrated in FIG. 1, the toilet device includes a sit-down flush toilet (for convenience of description hereinbelow, called simply the "toilet") 800 and a sanitary washing device 100 provided at the upper part of the toilet 800. The sanitary washing device 100 includes a casing 400, a toilet seat 200, and a toilet lid 300. The toilet seat 200 and the toilet lid 300 each are pivotally supported to be openable and closable with respect to the casing 400.

A private part washing functional unit that realizes the washing of a private part such as the "bottom" or the like of a user sitting on the toilet seat 200 and the like are provided inside the casing 400. For example, a seating detection sensor 404 that detects the user being seated on the toilet seat 200 is provided in the casing 400. When the seating detection sensor 404 detects the user sitting on the toilet seat 200, a private part washing nozzle (for convenience of description hereinbelow, called simply the "nozzle") 473 can be caused to advance into the toilet 800 (into a bowl 801) or retract from the interior of the bowl 801 when the user operates an operation part 500 such as, for example, a remote control, etc. (referring to FIG. 2). A state in which the nozzle 473 is advanced into the bowl 801 is illustrated in the sanitary washing device 100 illustrated in FIG. 1.

The nozzle 473 washes the human body private part by discharging water toward the human body private part. The nozzle 473 includes an outer tube 473a that is slidable in the longitudinal direction, and an inner tube 473b that is provided inside the outer tube 473a and is slidable in the longitudinal direction. In other words, the nozzle 473 is a two-stage nozzle in which the outer tube 473a and the inner tube 473b advance and retract in the longitudinal direction. A bidet wash water discharge port 474a and a bottom wash water discharge port 474b are provided in the tip portion of the inner tube 473b of the nozzle 473. The nozzle 473 can wash a female private part of a female sitting on the toilet seat 200 by squirting water from the bidet wash water discharge port 474a provided in the tip of the nozzle 473. The nozzle 473 also can wash the "bottom" of the user sitting on the toilet seat 200 by squirting water from the bottom wash water discharge port 474b provided in the tip of the nozzle 473. In this specification, "water" includes not only cold water but also warm water that is heated.

The modes of washing the "bottom" include, for example, a "bottom wash" and a "gentle wash" that gently washes using a water stream that is softer than that of the "bottom wash". For example, the nozzle 473 can perform the "bidet wash", the "bottom wash", and the "gentle wash".

Although the bidet wash water discharge port 474a is provided further toward the tip side of the nozzle 473 than the bottom wash water discharge port 474b in the nozzle 473 illustrated in FIG. 1, the mounting positions of the bidet wash water discharge port 474a and the bottom wash water discharge port 474b are not limited to the example. The bidet wash water discharge port 474a may be provided further toward the back end side of the nozzle 473 than the bottom wash water discharge port 474b. Although two water discharge ports are provided in the nozzle 473 illustrated in FIG. 1, three or more water discharge ports may be provided.

Figure 2:
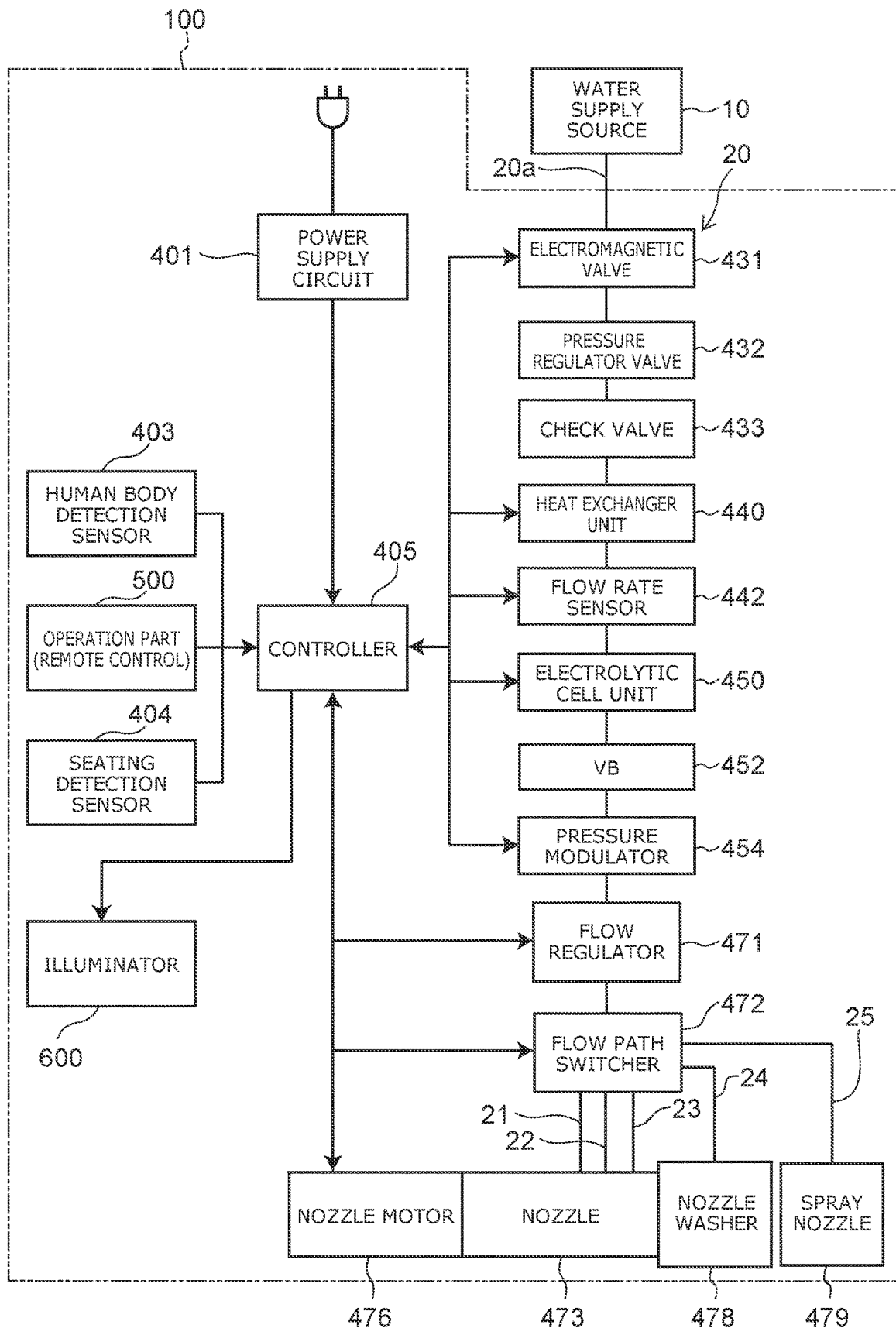
FIG. 2 is a block diagram illustrating the relevant components of the sanitary washing device.

FIG. 2 is a block diagram illustrating the relevant components of the sanitary washing device.

The relevant components of the water channel system and the electrical system are illustrated together in FIG. 2.

As illustrated in FIG. 2, the sanitary washing device 100 includes a water transfer part 20. The water transfer part 20 includes a pipe line 20a that reaches the nozzle 473 from a water supply source 10 such as a service water line, a water storage tank, etc. The water transfer part 20 guides the water supplied from the water supply source 10 to the nozzle 473 via the pipe line 20a. For example, the pipe line 20a is formed of components such as an electromagnetic valve 431, a heat exchanger unit 440, a flow path switcher 472, etc., which are described below, and multiple piping that connects these components.

The electromagnetic valve 431 is provided at the upstream side of the water transfer part 20. The electromagnetic valve 431 is an openable and closeable electromagnetic valve and controls the supply of the water based on a command from a controller 405 provided inside the casing 400. In other words, the electromagnetic valve 431 opens and closes the pipe line 20a. The water that is supplied from the water supply source 10 is caused to flow in the pipe line 20a by setting the electromagnetic valve 431 to the open state.

A pressure regulator valve 432 is provided downstream of the electromagnetic valve 431. The pressure regulator valve 432 regulates the pressure inside the pipe line 20a to be in a prescribed pressure range when the water supply pressure is high. A check valve 433 is provided downstream of the pressure regulator valve 432. The check valve 433 suppresses the backflow of water toward the upstream side of the check valve 433 when the pressure inside the pipe line 20a decreases, etc.

The heat exchanger unit 440 (the heater) is provided downstream of the check valve 433. The heat exchanger unit 440 includes a heater and heats the water supplied from the water supply source 10 to, for example, a specified temperature. In other words, the heat exchanger unit 440 produces warm water.

The heat exchanger unit 440 is, for example, an instant heating-type (instantaneous-type) heat exchanger that uses a ceramic heater, etc. Compared to a warm water storage heating-type heat exchanger that uses a warm water storage tank, the instant heating-type heat exchanger can heat the water to the specified temperature in a short period of time. The heat exchanger unit 440 is not limited to an instant heating-type heat exchanger and may be a warm water storage heating-type heat exchanger. The heater is not limited to a heat exchanger; for example, another heating technique such as one that utilizes microwave heating, etc., may be used.

The heat exchanger unit 440 is connected to the controller 405. For example, the controller 405 heats the water to the temperature set by the operation part 500 by controlling the heat exchanger unit 440 according to an operation of the operation part 500 by the user.

A flow rate sensor 442 is provided downstream of the heat exchanger unit 440. The flow rate sensor 442 detects the flow rate of the water discharged from the heat exchanger unit 440. In other words, the flow rate sensor 442 detects the flow rate of the water flowing through the pipe line 20a. The flow rate sensor 442 is connected to the controller 405. The flow rate sensor 442 inputs the detection result of the flow rate to the controller 405.

An electrolytic cell unit 450 is provided downstream of the flow rate sensor 442. The electrolytic cell unit 450 generates a liquid (functional water) including hypochlorous acid from the service water by electrolyzing the service water flowing through the interior of the electrolytic cell unit 450. The electrolytic cell unit 450 is connected to the controller 405. The electrolytic cell unit 450 is included in the sterilizing water generator of the invention and generates the sterilizing water (the functional water) based on a control by the controller 405.

The functional water that is generated by the electrolytic cell unit 450 may be, for example, a solution including metal ions such as silver ions, copper ions, etc. Or, the functional water that is generated by the electrolytic cell unit 450 may be a solution including electrolytic chlorine, ozone, etc. Or, the functional water that is generated by the electrolytic cell unit 450 may be acidic water or alkaline water. The electrolytic cell unit 450 supplies the sterilizing water (the functional water) to the bidet wash water discharge port 474a of the nozzle 473 and/or the bottom wash water discharge port 474b and a water discharger 478a of a nozzle washer 478.

A vacuum breaker (VB) 452 is provided downstream of the electrolytic cell unit 450. The vacuum breaker 452 includes, for example, a flow channel for allowing the water to flow, an intake port for intaking air into the flow channel, and a valve mechanism that opens and closes the intake port. For example, the valve mechanism blocks the intake port when water is flowing in the flow channel and intakes air into the flow channel by opening the intake port when the flow of the water stops. In other words, the vacuum breaker 452 intakes air into the pipe line 20a when the water does not flow in the water transfer part 20. The valve mechanism includes, for example, a float valve.

As described above, the vacuum breaker 452 intakes air into the pipe line 20a, thereby promoting, for example, water drainage of the portion of the pipe line 20a downstream of the vacuum breaker 452. For example, the vacuum breaker 452 promotes the water drainage of the nozzle 473. Thus, the vacuum breaker 452 drains the water inside the nozzle 473 and intakes air into the nozzle 473, thereby suppressing, for example, the undesirable backflow toward the water supply source 10 (the fresh water) side of the wash water inside the nozzle 473, the liquid waste collected inside the bowl 801, etc.

A pressure modulator 454 is provided downstream of the vacuum breaker 452. The pressure modulator 454 applies a pulsatory motion to the water discharged from the bidet wash water discharge port 474a and the bottom wash water discharge port 474b of the nozzle 473 and/or the water discharger 478a of the nozzle washer 478 by applying a pulsatory motion or an acceleration to the flow of the water inside the pipe line 20a of the water transfer part 20. In other words, the pressure modulator 454 causes the fluidic state of the water flowing through the pipe line 20a to fluctuate. The pressure modulator 454 is connected to the controller 405. The pressure modulator 454 causes the fluidic state of the water to fluctuate based on a control by the controller 405. The pressure modulator 454 causes the pressure of the water inside the pipe line 20a to fluctuate.

A flow regulator 471 is provided downstream of the pressure modulator 454. The flow regulator 471 regulates the water force (the flow rate). The flow path switcher 472 is provided downstream of the flow regulator 471. The flow path switcher 472 performs opening and closing and switching of the water supply to the nozzle 473 and/or the nozzle washer 478. The flow regulator 471 and the flow path switcher 472 may be provided as one unit. The flow regulator 471 and the flow path switcher 472 are connected to the controller 405. The operations of the flow regulator 471 and the flow path switcher 472 are controlled by the controller 405.

The nozzle 473, the nozzle washer 478, and a spray nozzle 479 are provided downstream of the flow path switcher 472. The nozzle 473 receives a drive force from a nozzle motor 476, advances into the bowl 801 of the toilet 800, and retracts from the interior of the bowl 801. That is, the nozzle motor 476 is a drive device that causes the nozzle 473 to advance and retract based on a command from the controller 405.

The nozzle washer 478 washes and sterilizes the outer circumferential surface (the central body) of the inner tube 473b of the nozzle 473 by squirting sterilizing water (functional water) from the water discharger 478a. The nozzle washer 478 may wash the outer circumferential surface (the central body) of the inner tube 473b of the nozzle 473 by squirting water from the water discharger 478a. The nozzle washer 478 also may wash and sterilize the outer circumferential surface of the outer tube 473a of the nozzle 473. The spray nozzle 479 sprays the water or the functional water into the bowl 801 in a mist form. In the example, the spray nozzle 479 is provided separately from the nozzle 473 for washing the human body. The spraying is not limited thereto; a water discharge port for spraying a mist-like liquid into the bowl 801 may be provided in the nozzle 473.

A bottom wash channel 21, a gentle wash channel 22, and a bidet wash channel 23 also are provided downstream of the flow path switcher 472. The bottom wash channel 21 and the gentle wash channel 22 guide, toward the bottom wash water discharge port 474b, the water supplied from the water supply source 10 or the functional water generated by the electrolytic cell unit 450 via the water transfer part 20. The bidet wash channel 23 guides, toward the bidet wash water discharge port 474a, the water supplied from the water supply source 10 or the functional water generated by the electrolytic cell unit 450 via the water transfer part 20.

A surface wash channel 24 and a spray channel 25 also are provided downstream of the flow path switcher 472. The surface wash channel 24 guides, toward the water discharger 478a of the nozzle washer 478, the water supplied from the water supply source 10 or the functional water generated by the electrolytic cell unit 450 via the water transfer part 20. The spray channel 25 guides, toward the spray nozzle 479, the water supplied from the water supply source 10 or the functional water generated by the electrolytic cell unit 450 via the water transfer part 20.

By controlling the flow path switcher 472, the controller 405 switches the opening and closing of the flow channels of the bottom wash channel 21, the gentle wash channel 22, the bidet wash channel 23, the surface wash channel 24, and the spray channel 25. Thus, the flow path switcher 472 switches between the state of communicating with the pipe line 20a and the state of not communicating with the pipe line 20a for each of the multiple water discharge ports of the bidet wash water discharge port 474a, the bottom wash water discharge port 474b, the nozzle washer 478, the spray nozzle 479, etc.

The controller 405 is supplied with electrical power from a power supply circuit 401 and controls the operations of the electromagnetic valve 431, the heat exchanger unit 440, the electrolytic cell unit 450, the pressure modulator 454, the flow regulator 471, the flow path switcher 472, the nozzle motor 476, etc., based on signals from a human body detection sensor 403, the seating detection sensor 404, the flow rate sensor 442, the operation part 500, etc.

For example, the controller 405 also controls an illuminator 600 based on detection information of the human body detection sensor 403 and/or the seating detection sensor 404. The illuminator 600 irradiates sterilizing light, which is light having a sterilizing action, on the periphery of the nozzle 473 (a nozzle storage part 480 described below, etc.). The illuminator 600 is described below.

As illustrated in FIG. 1, the human body detection sensor 403 is sunk into a recessed portion 409 formed in the upper surface of the casing 400 and detects the user (the human body) approaching the toilet seat 200. In other words, the human body detection sensor 403 detects the user at the vicinity of the sanitary washing device 100. A transmissive window 310 is provided at the back part of the toilet lid 300. Therefore, the human body detection sensor 403 can detect the existence of the user via the transmissive window 310 in the state in which the toilet lid 300 is closed. For example, the controller 405 responds to the detection of the user by the human body detection sensor 403 by automatically opening the toilet lid 300.

Various mechanisms such as a "deodorizing unit", a "room heating unit", a "warm air drying function" that dries the "bottom" or the like of the user sitting on the toilet seat 200 by blowing warm air toward the "bottom" or the like, etc., also may be provided as appropriate in the casing 400. In such a case, an exhaust port 407 from the deodorizing unit and a vent 408 from the room heating unit are provided as appropriate in the side surface of the casing 400. However, in the invention, the sanitary washing functional units or the other additional functional units may not always be provided.

Figure 3:
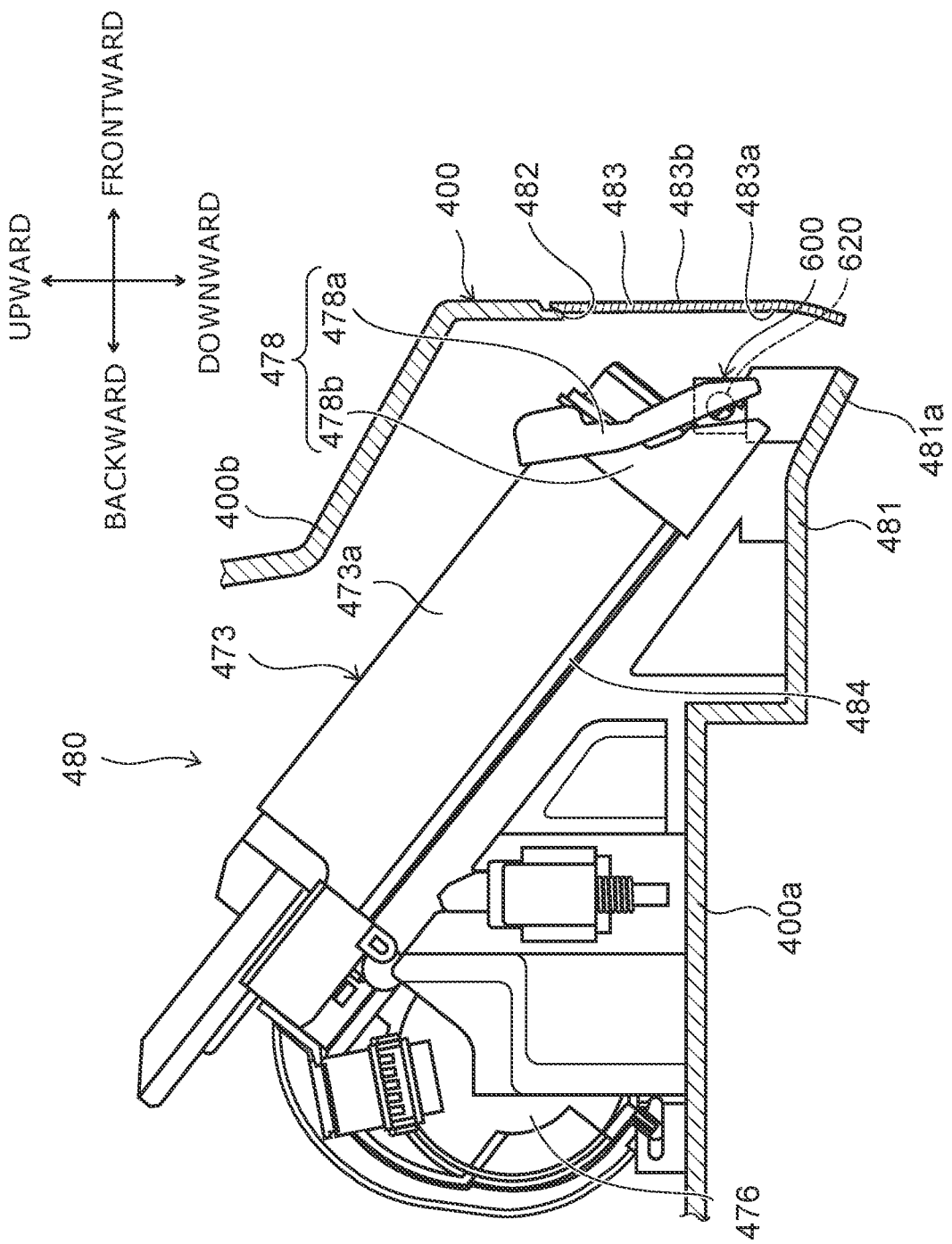
FIG. 3 is a cross-sectional view illustrating a state in which the private part washing nozzle is retracted into the casing.

FIG. 3 is a cross-sectional view illustrating a state in which the private part washing nozzle is retracted into the casing.

Figure 4:
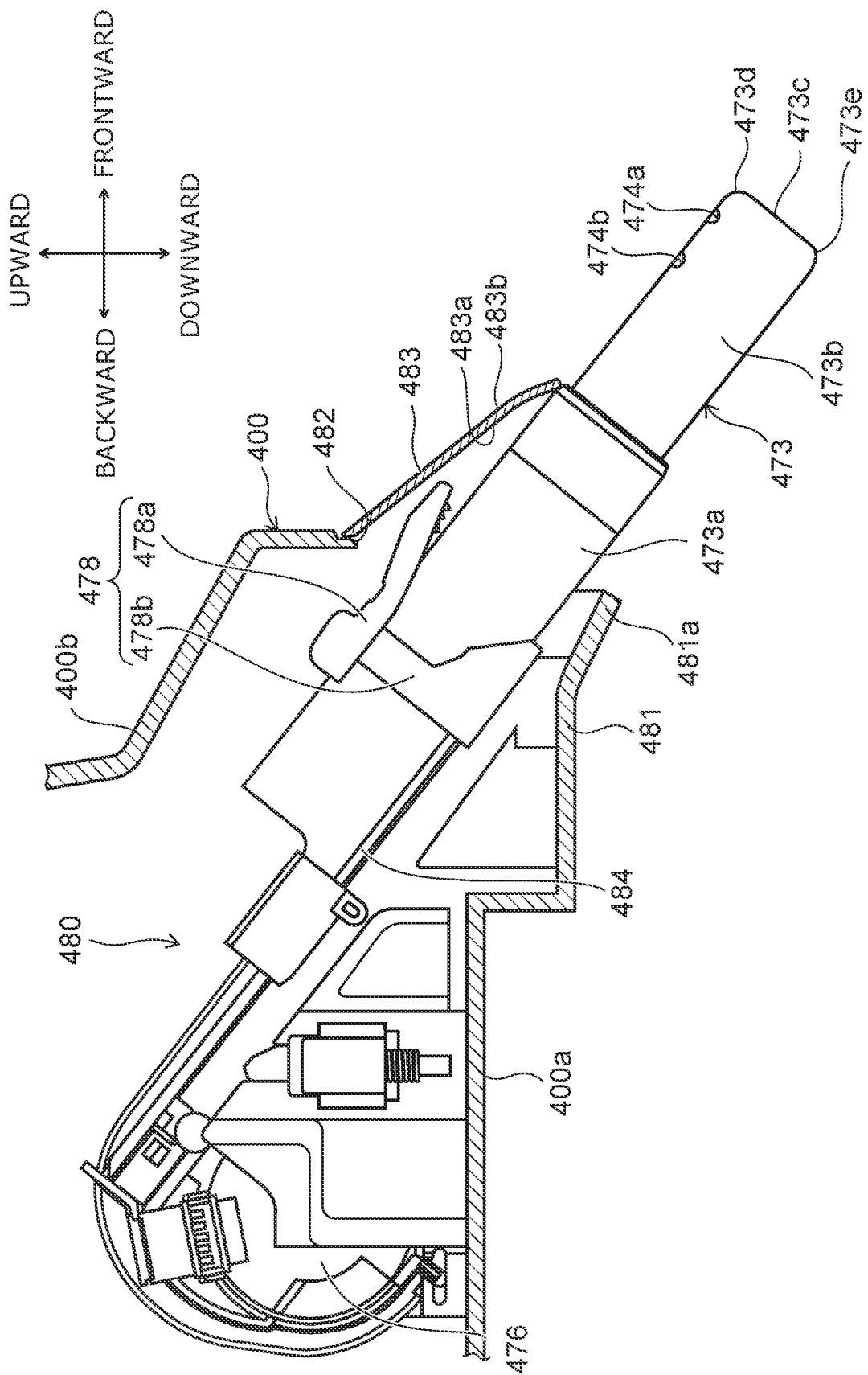
FIG. 4 is a cross-sectional view illustrating a state in which the private part washing nozzle is advanced from the interior of the casing.

FIG. 4 is a cross-sectional view illustrating a state in which the private part washing nozzle is advanced from the interior of the casing.

Figure 5:
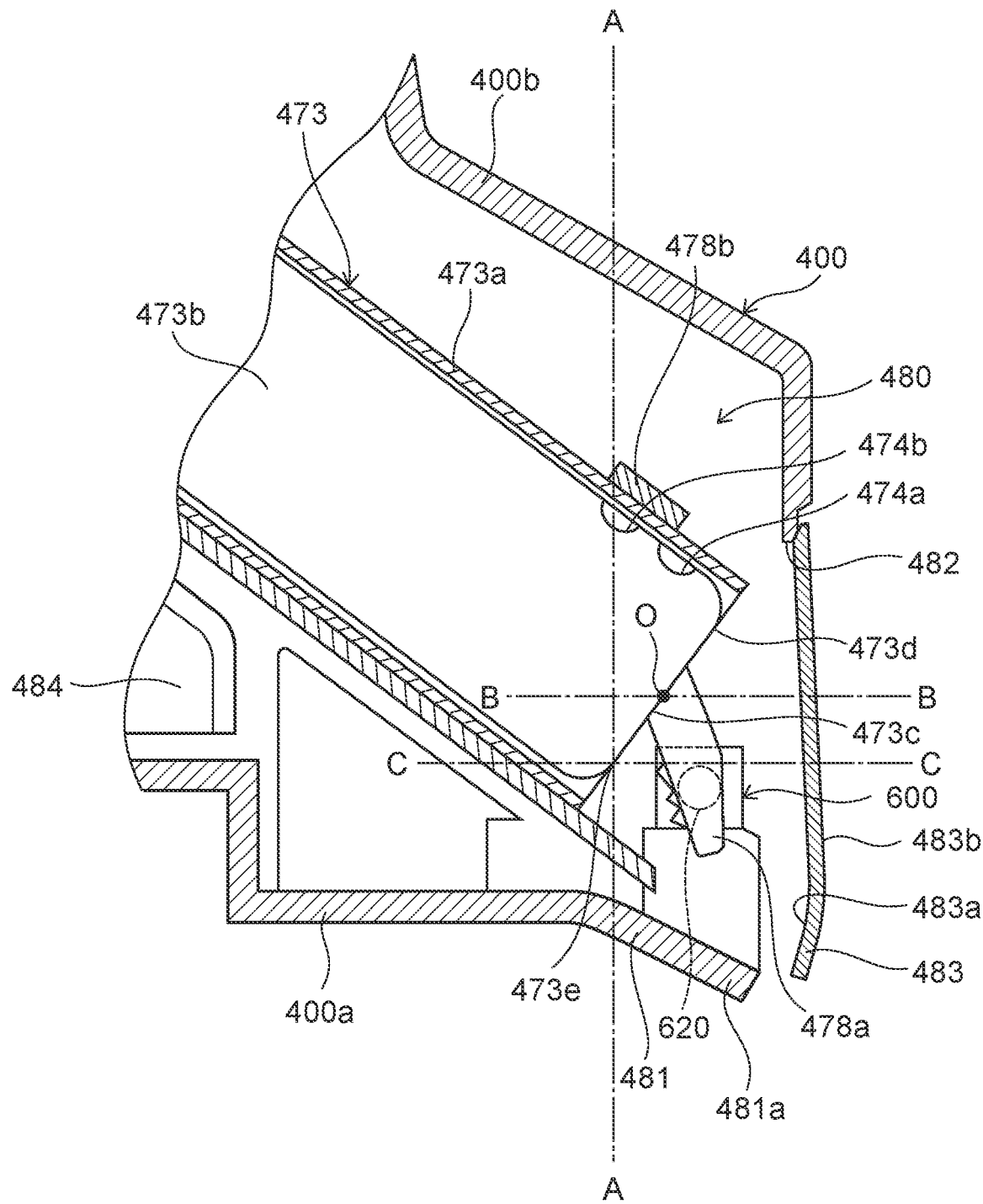
FIG. 5 is an enlarged cross-sectional view of the front end side of the private part washing nozzle of FIG. 3 illustrating the inner tube of the private part washing nozzle.

FIG. 5 is an enlarged cross-sectional view of the front end side of the private part washing nozzle of FIG. 3 illustrating the inner tube of the private part washing nozzle.

Figure 6:
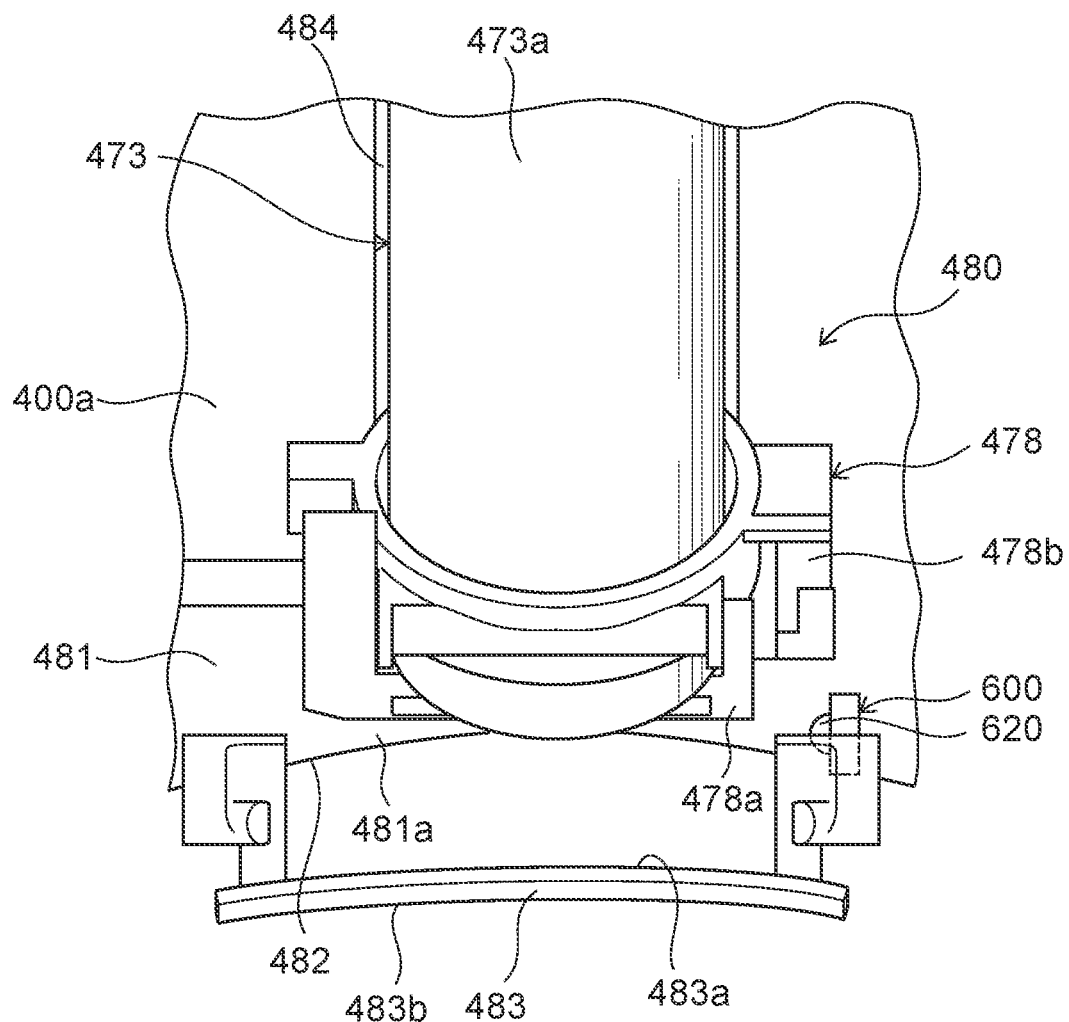
FIG. 6 is a plan view illustrating the private part washing nozzle periphery.

FIG. 6 is a plan view illustrating the private part washing nozzle periphery.

Figure 7A:
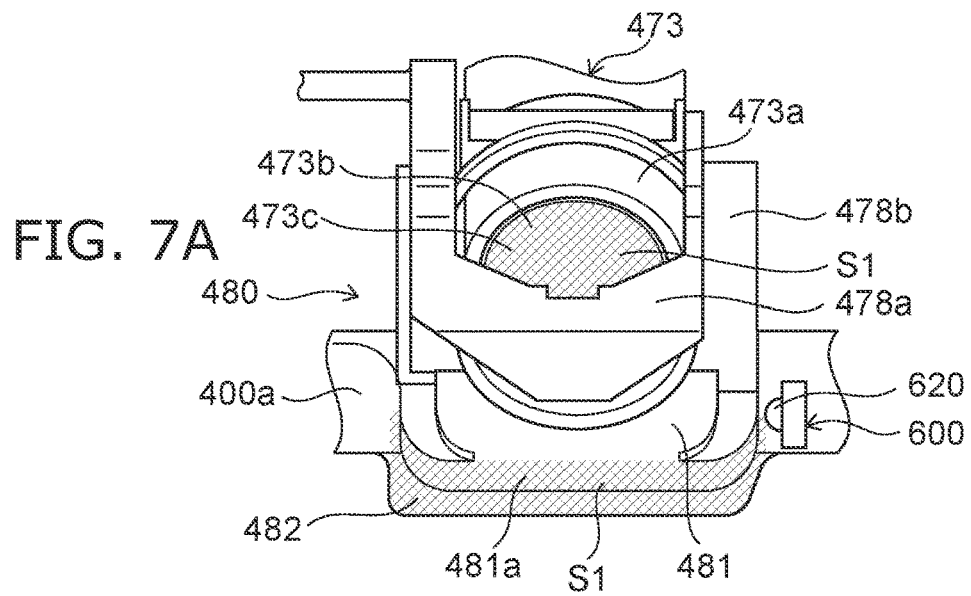
FIGS. 7A to 7C are explanatory drawings illustrating the areas of the private part washing nozzle and the nozzle storage part sterilized by the sterilizing water.
Figure 7B:
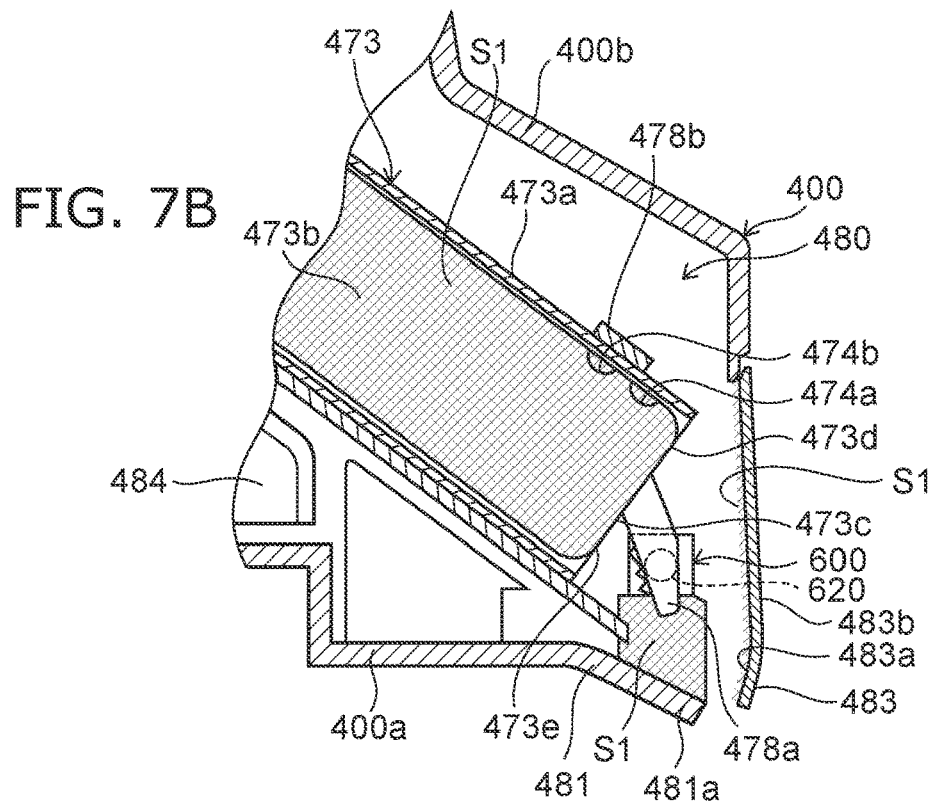
Figure 7C:
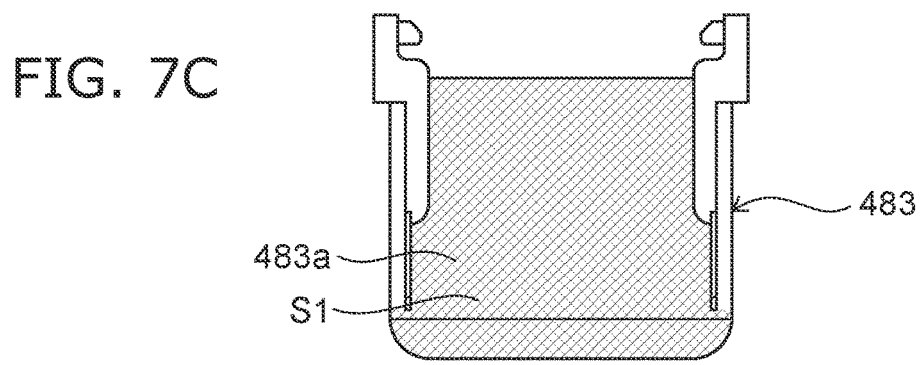

FIGS. 7A to 7C are explanatory drawings illustrating the areas of the private part washing nozzle and the nozzle storage part sterilized by the sterilizing water. FIG. 7A is a front view of the private part washing nozzle and the nozzle storage part when viewed from the front. The nozzle lid is not illustrated in FIG. 7A. FIG. 7B is a cross-sectional view of the private part washing nozzle and the nozzle storage part when viewed from the side. FIG. 7C is a back view illustrating the inner surface side of the nozzle lid.

Figure 8A:
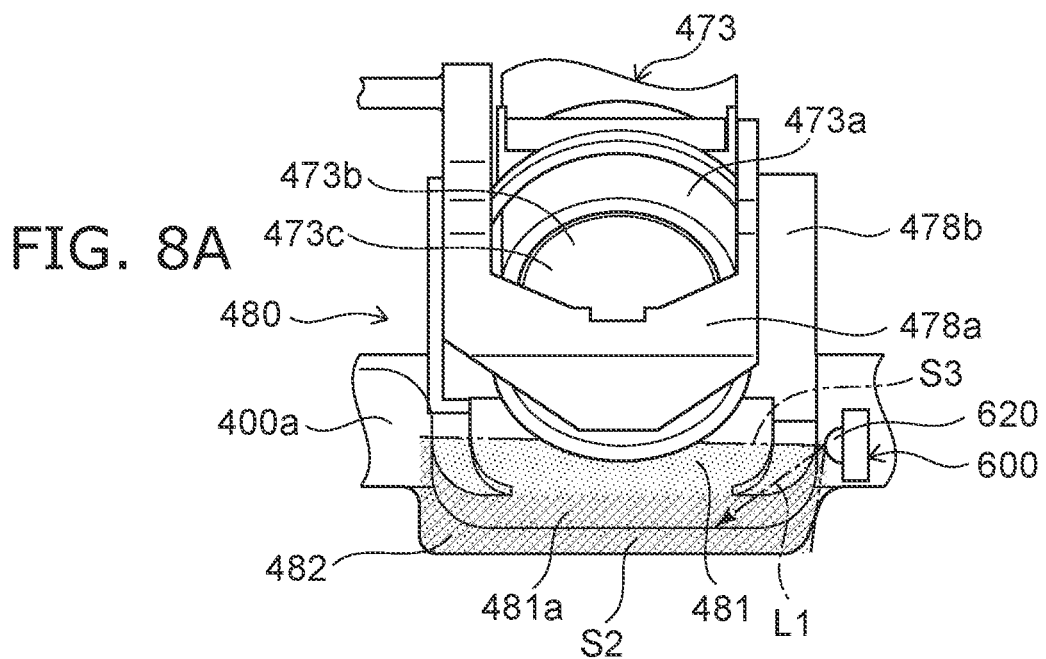
FIGS. 8A and 8B are explanatory drawings illustrating an example of the residual water occurrence portion of the sterilizing water remaining in the nozzle storage part and the sterilizing light irradiated on the residual water occurrence portion.
Figure 8B:
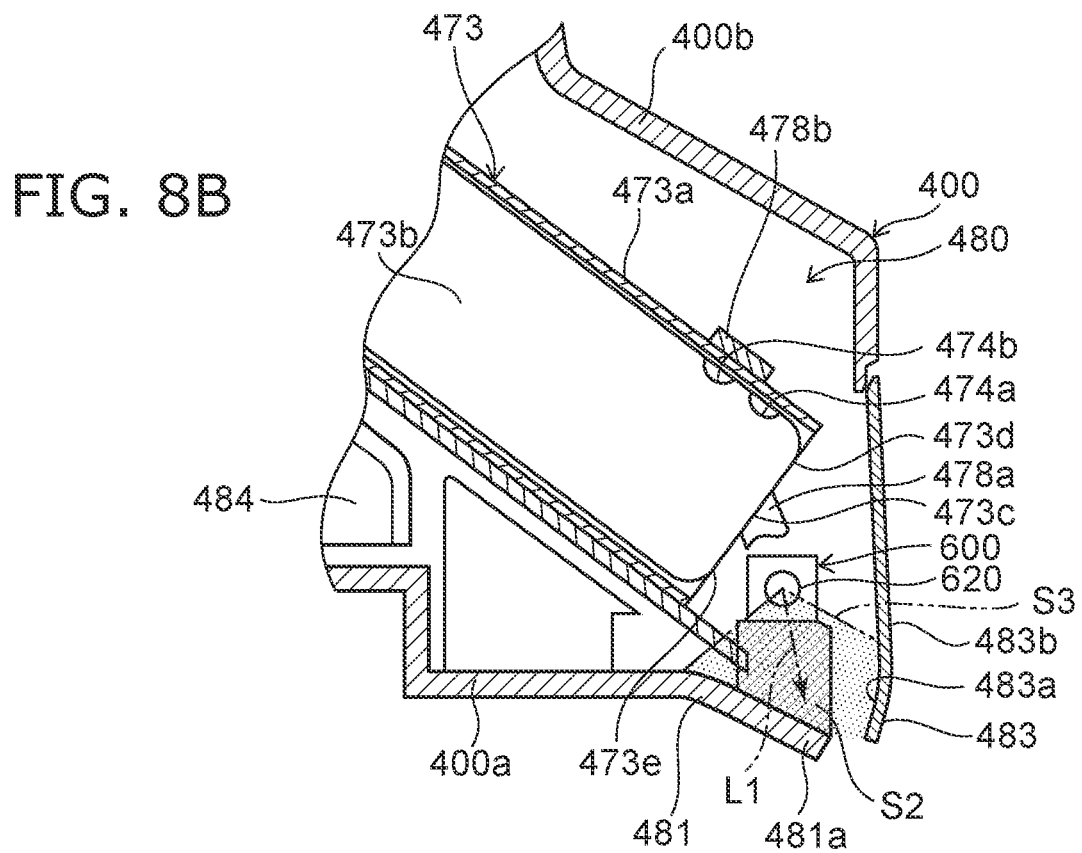

FIGS. 8A and 8B are explanatory drawings illustrating an example of the residual water occurrence portion of the sterilizing water remaining in the nozzle storage part and the sterilizing light irradiated on the residual water occurrence portion. FIG. 8A is a front view of the private part washing nozzle and the nozzle storage part when viewed from the front. The nozzle lid is not illustrated in FIG. 8A. FIG. 8B is a cross-sectional view of the private part washing nozzle and the nozzle storage part when viewed from the side. The tip side of the water discharger 478a is not illustrated for convenience of description in FIG. 8B.

As illustrated in FIGS. 3 and 5, the casing 400 includes the nozzle storage part 480 that is configured to store the entire nozzle 473 in the state in which the nozzle 473 is retracted. In other words, the nozzle storage part 480 is the portion of the interior of the casing 400 in which the nozzle 473 is stored.

The nozzle storage part 480 includes a nozzle lid 483 that is configured to open and close an opening 482 provided at the front end of the nozzle storage part 480, and a bottom portion 481 of a case plate 400a, which forms the bottom surface of the casing 400, positioned below the nozzle 473. The nozzle lid 483 may not be provided. The nozzle storage part 480 is covered with a case cover 400b from above. A nozzle supporter 484 that supports the nozzle 473 to be advanceable and retractable is provided in the nozzle storage part 480.

The nozzle storage part 480 is sterilized by the sterilizing water discharged from the water discharger 478a of the nozzle washer 478 and the sterilizing light irradiated from the illuminator 600 described below. The interior of the nozzle storage part 480 is washed and sterilized by the sterilizing water being supplied (flowing) into the nozzle storage part 480. As in the lattice-like hatching shown in FIGS. 7A to 7C, a sterilizing water area S1 is a wide area of the bottom portion 481 of the nozzle storage part 480, an inner surface 483a of the nozzle lid 483, etc., in addition to the outer circumferential surface (the central body) of the nozzle 473.

The bottom portion 481 is tilted into the bowl 801 of the toilet 800. Thereby, the sterilizing water flows down from a front end 481a of the bottom portion 481 into the bowl 801 of the toilet 800. In such a case, the sterilizing water may remain inside the nozzle storage part 480 due to, for example, the materials and the configuration of the nozzle storage part 480, the surface tension of the sterilizing water, etc.

For example, due to surface tension, the sterilizing water easily remains at the front end 481a side of the bottom portion 481 without dropping into the toilet 800. Concentration decay of the sterilizing water remaining in the nozzle storage part 480 progresses over time. Accordingly, the residual water occurrence portion at which the sterilizing water remains becomes an environment in which bacteria and/or mold easily occur. In such a case, the residual water occurrence portion can be designated by, for example, designating the area (the flow channel) through which the sterilizing water flows and by confirming the occurrence degree of bacteria and/or mold when left idle for a prescribed period. In the embodiment, the front end 481a side of the bottom portion 481 of the nozzle storage part 480 is taken as a residual water occurrence portion S2 in which the sterilizing water easily remains. Although the entire front end 481a side of the bottom portion 481 is taken as the residual water occurrence portion S2 in FIGS. 8A and 8B, a part of the front end 481a side of the bottom portion 481 may be taken as the residual water occurrence portion S2. The sterilizing light is irradiated on the residual water occurrence portion S2 from the illuminator 600 described below.

The nozzle supporter 484 supports the nozzle 473 below the nozzle 473. The nozzle supporter 484 is tilted downward along a direction from the back toward the front. The nozzle 473 advances and retracts while sliding with respect to the nozzle supporter 484. For example, a tubular member that stores the nozzle 473 may be provided in the nozzle storage part 480.

The nozzle washer 478 is mounted to the front end of the nozzle supporter 484. As illustrated in FIGS. 3 and 4, the nozzle washer 478 includes the water discharger 478a, in which a water discharge hole that discharges sterilizing water and/or water is formed, and a support body 478b of the water discharger 478a. The opening 482 is provided in the front end of the nozzle storage part 480. The opening 482 is provided in the lower side of the front surface of the casing 400. The nozzle washer 478 is positioned backward of the opening 482. For example, the nozzle washer 478 washes the outer circumferential surface (the central body) of the nozzle 473 by squirting sterilizing water and/or water from the water discharger 478a when the nozzle 473 advances and retracts.

The nozzle lid 483 is provided frontward of the nozzle 473. The nozzle lid 483 is pivotally supported by the case cover 400b of the casing 400 and is configured to open and close the opening 482 of the front surface of the case cover 400b provided at the front end of the nozzle storage part 480. The nozzle lid 483 is in an open state in which the opening 482 is open when the nozzle 473 is advanced as illustrated in FIG. 4, and the nozzle lid 483 is in a closed state in which the opening 482 is closed when the entire nozzle 473 is stored in the nozzle storage part 480 as illustrated in FIG. 3. For example, the opening 482 is blocked by the nozzle lid 483 when the nozzle lid 483 is in the closed state.

The nozzle lid 483 includes the inner surface 483a and an outer surface 483b. The inner surface 483a is positioned inside the nozzle storage part 480 (at the nozzle 473 side) in the closed state. The outer surface 483b is positioned at the side opposite to the inner surface 483a (the interior side of the toilet 800). In other words, the inner surface 483a is positioned backward in the closed state, and the outer surface 483b is positioned frontward in the closed state.

When the nozzle 473 is not used, the nozzle 473 is stored in the nozzle storage part 480 in a state in which the inner tube 473b is positioned inside the outer tube 473a as illustrated in FIGS. 3 and 5. When the private part wash is performed by the nozzle 473, the nozzle 473 slides frontward and downward with respect to the nozzle storage part 480. When the nozzle 473 slides frontward and downward, the nozzle 473 contacts the nozzle washer 478, and the nozzle lid 483 and the water discharger 478a of the nozzle washer 478 are pushed upward. For example, the nozzle 473 is washed by discharging water from the water discharger 478a until the nozzle 473 reaches a prescribed position.

When the nozzle 473 reaches a prescribed position as illustrated in FIG. 4, the inner tube 473b protrudes from the outer tube 473a. Then, water is discharged from the bidet wash water discharge port 474a or the bottom wash water discharge port 474b of the inner tube 473b toward the private part of the user, and washing is performed. When the private part wash is completed, the nozzle 473 slides backward and upward toward the nozzle storage part 480. For example, the nozzle 473 is washed and sterilized by the sterilizing water discharged from the water discharger 478a until the nozzle 473 is stored in the nozzle storage part 480. In such a case, the sterilizing water that is discharged from the water discharger 478a contacts the bottom portion 481 of the nozzle storage part 480 and the inner surface 483a of the nozzle lid 483 and flows down into the toilet 800 (into the bowl 801). Accordingly, the sterilizing water also sterilizes the interior of the nozzle storage part 480.

The illuminator 600 irradiates sterilizing light, which has a sterilizing action, into the nozzle storage part 480. As illustrated in FIG. 3, for example, the illuminator 600 is positioned inside the casing 400 and is located above the bottom portion 481. In the example as illustrated in FIGS. 5 and 6, the illuminator 600 is located at one lateral-direction side (the left side) below the nozzle supporter 484 and irradiates sterilizing light toward the other lateral-direction side (the right side). The illuminator 600 may be located at the right side and may irradiate the sterilizing light toward the left side.

Here, as a first condition, at least a part of the illuminator 600 is located further frontward than a front surface 473c of the nozzle 473 in the state in which the nozzle 473 is retracted. In other words, as illustrated in FIG. 5, because the front surface 473c of the nozzle 473 is tilted backward from an upper end 473d toward a lower end 473e, the at least a part of the illuminator 600 is located further frontward than a virtual line A-A extending in the vertical direction and passing through the lower end 473e of the front surface 473c.

As a second condition, at least a part of the illuminator 600 is located lower than a center O of the front surface 473c of the nozzle 473 in the state in which the nozzle 473 is retracted. In other words, as illustrated in FIG. 5, the at least a part of the illuminator 600 is located lower than a virtual line B-B extending in the longitudinal direction and passing through the center O of the front surface 473c.

As a third condition, at least a part of the illuminator 600 is located higher than the lower end 473e of the front surface 473c of the nozzle 473 in the state in which the nozzle 473 is retracted. In other words, as illustrated in FIG. 5, the at least a part of the illuminator 600 is located higher than a virtual line C-C extending in the longitudinal direction and passing through the lower end 473e of the front surface 473c.

By satisfying one of the first to third conditions, the illuminator 600 can be proximate to the residual water occurrence portion S2. Accordingly, the irradiation intensity of the illuminator 600 on the residual water occurrence portion (e.g., the residual water occurrence portion S2) can be increased, and the occurrence of bacteria and/or mold in the residual water occurrence portion S2 can be suppressed. In the embodiment, the illuminator 600 is located at a position that satisfies all of the first to third conditions.

As illustrated in FIGS. 8A and 8B, the illuminator 600 irradiates sterilizing light toward the residual water occurrence portion S2, at which the sterilizing water that flows through the nozzle storage part 480 remains. At least a portion of the bacteria adhered to the residual water occurrence portion S2 is sterilized by being annihilated or deactivated by the irradiation of the sterilizing light. In such a case, for example, the illuminator 600 directs the sterilizing light toward the residual water occurrence portion S2. The direction in which the sterilizing light is directed can be considered to be the direction in which the intensity of the sterilizing light is a maximum. Thus, the illuminator 600 can effectively sterilize the residual water occurrence portion by directing, toward the residual water occurrence portion S2, an optical axis L1 of the maximum intensity of the sterilizing light having an irradiation area S3 shown by the double dot-dash lines in FIGS. 8A and 8B.

For example, the optical axis L1 at which the intensity is greatest is the center of the irradiation width of the sterilizing light (the central axis of the divergence angle). There may be multiple optical axes at which the intensity is greatest when a lens or the like is provided frontward of the illuminator 600. In such a case, it is sufficient for at least one optical axis of the multiple optical axes to be directed toward the residual water occurrence portion S2.

The illuminator 600 includes, for example, a light-emitting element 620 (a light-emitting body). The light-emitting element 620 is, for example, an LED (Light Emitting Diode). The light-emitting element 620 is not limited to an LED and may be, for example, a LD (Laser Diode), an OLED (Organic Light Emitting Diode), etc. The light-emitting element 620 may be, for example, a cold cathode fluorescent tube or a hot cathode fluorescent tube. The wavelength of the sterilizing light radiated by the light-emitting element 620 is, for example, 250 nm to 480 nm.

The light-emitting element 620 is connected to the controller 405 via a substrate and is lit and unlit based on a control of the controller 405. The controller 405 controls the operation of the illuminator 600 by controlling the light-emitting element 620 to be lit or unlit. The controller 405 also may control the radiant intensity of the light-emitting element 620 by adjusting the voltage applied to the light-emitting element 620.

The sanitary washing device 100 according to the embodiment has a configuration such as that described above; the sterilization of the nozzle 473 and the nozzle storage part 480 by the sterilizing water and the sterilizing light will now be described.

For example, when the user that is seated on the toilet seat 200 operates the operation part 500 (the remote control), the nozzle 473 reaches the prescribed position. Subsequently, the private part wash is performed by discharging water from the bidet wash water discharge port 474a or the bottom wash water discharge port 474b toward the private part of the user. When the private part wash is completed, the nozzle 473 slides backward and upward toward the nozzle storage part 480.

Then, the outer circumferential surface of the nozzle 473 is washed and sterilized by the sterilizing water discharged from the water discharger 478a being supplied to the nozzle 473 until the nozzle 473 is stored in the nozzle storage part 480. After the nozzle 473 has retracted, the bidet wash water discharge port 474a and the bottom wash water discharge port 474b are washed and sterilized (self-cleaned) by discharging sterilizing water and water from a bidet wash water discharge port 474a and/or the bottom wash water discharge port 474b of the nozzle 473. In such a case, the sterilizing water flows through the nozzle storage part 480 and flows down into the toilet 800 (into the bowl 801) from the opening 482. Accordingly, in addition to the nozzle 473, the sterilizing water also sterilizes the inner surface of the nozzle storage part 480, the bottom portion 481, and the inner surface 483a of the nozzle lid 483. In other words, as illustrated in the sterilizing water area S1 in FIGS. 7A to 7C, the sterilizing water can sterilize a wide area of the nozzle 473 and the interior of the nozzle storage part 480.

Nearly all of the sterilizing water supplied into the nozzle storage part 480 flows down into the bowl 801 of the toilet 800 from the opening 482. However, as illustrated in the residual water occurrence portion S2 in FIGS. 8A and 8B, for example, the sterilizing water easily remains at the front end 481a side of the bottom portion 481 of the nozzle storage part 480 due to the surface tension of the sterilizing water, etc. In the residual water occurrence portion S2, concentration decay progresses over time. Thereby, the residual water occurrence portion S2 undesirably becomes an environment in which bacteria and/or mold easily occur.

Therefore, in the embodiment, the illuminator 600 irradiates the sterilizing light toward the residual water occurrence portion S2. The illuminator 600 irradiates the sterilizing light toward the residual water occurrence portion S2 in the prescribed irradiation area S3. Favorably, the illuminator 600 irradiates with the optical axis L1 at which the intensity is greatest (the maximum beam direction) directed toward the residual water occurrence portion S2. The optical axis L1 at which the intensity is greatest is, for example, the center of the irradiation width of the sterilizing light (the central axis of the divergence angle). The occurrence of bacteria and/or mold at the residual water occurrence portion S2 can be suppressed thereby because the illuminator 600 can irradiate the sterilizing light with a high intensity toward the residual water occurrence portion S2. The illuminator 600 may not direct the maximum beam direction toward the residual water occurrence portion S2; it is sufficient for a portion of the sterilizing light to be irradiated on the residual water occurrence portion S2.

Thus, the sterilizing water can sterilize a wide area interior of the nozzle storage part 480. On the other hand, the sterilizing light is irradiated on the residual water occurrence portion S2 of the sterilizing water. In other words, the sterilizing light sterilizes a narrower area than the area sterilized by the sterilizing water. In other words, the sterilizing light suppresses the propagation of bacteria and/or mold having a risk of occurring due to the residual water of the sterilizing water. Accordingly, even when many illuminators 600, reflective materials, etc., are not provided, the clean state of the nozzle 473 and the nozzle storage part 480 can be efficiently maintained using the sterilizing water and the sterilizing light, and the enlargement of the casing 400 can be suppressed because the number of components can be as low as much as possible.

The illuminator 600 is positioned at the side of the opening 482 of the nozzle storage part 480 and irradiates the sterilizing light across the opening 482. Accordingly, the illuminator 600 can efficiently irradiate the sterilizing light toward the residual water extending in the lateral direction.

Figure 9A:
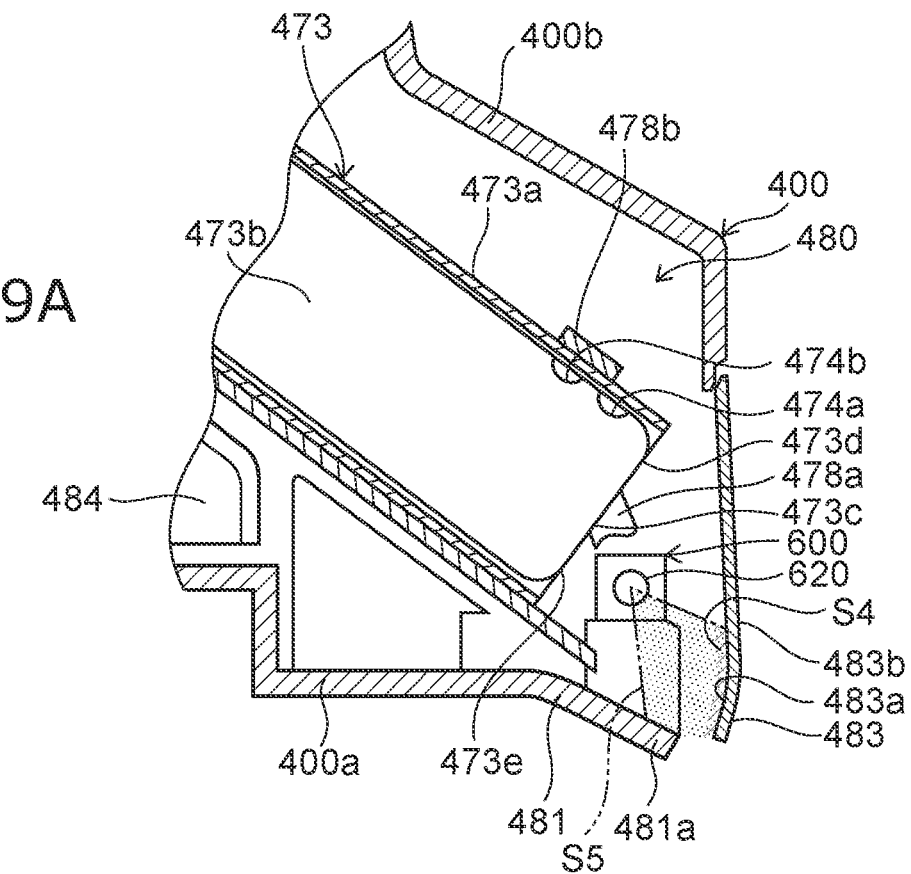
FIGS. 9A and 9B are explanatory drawings illustrating an example of the residual water occurrence portion of the sterilizing water remaining at the nozzle lid of the nozzle storage part and the sterilizing light irradiated on the residual water occurrence portion according to the first modification.
Figure 9B:
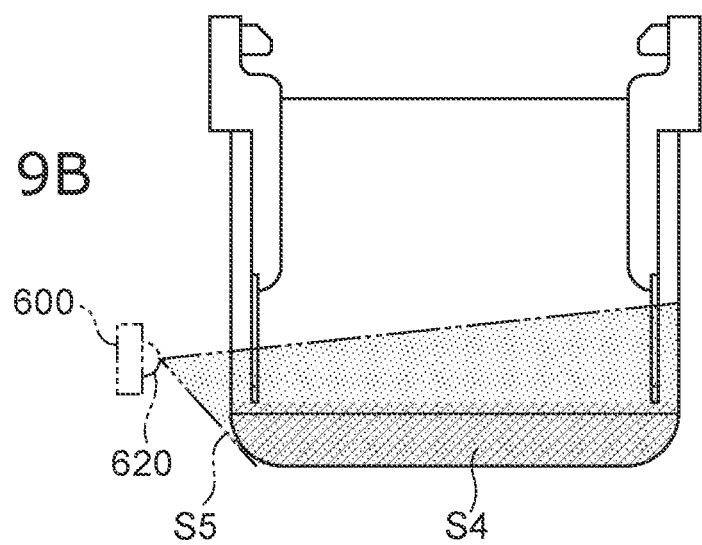

FIGS. 9A and 9B are explanatory drawings illustrating an example of the residual water occurrence portion of the sterilizing water remaining at the nozzle lid of the nozzle storage part and the sterilizing light irradiated on the residual water occurrence portion according to the first modification. FIG. 9A is a cross-sectional view of the nozzle and the nozzle storage part when viewed from the side. FIG. 9B is a back view illustrating the inner surface side of the nozzle lid.

An example is described in the embodiment described above in which the residual water occurrence portion S2 is the front end side of the bottom portion 481 of the nozzle storage part 480, and the sterilizing light is irradiated on the residual water occurrence portion S2. However, the invention is not limited thereto; the illuminator 600 may irradiate the sterilizing light on another residual water occurrence portion. For example, the sterilizing light may be irradiated on the nozzle washer 478 inside the nozzle storage part 480. The residual water occurrence portion can be determined by performing experiments and simulations using the materials and the configurations of the nozzle storage part 480 and the components inside the nozzle storage part 480, the flow rate of the sterilizing water, etc.

For example, as in the first modification illustrated in FIGS. 9A and 9B, the lower end side of the inner surface 483a of the nozzle lid 483 may be taken as a residual water occurrence portion S4 (the lattice-like hatching in FIGS. 9A and 9B). Although the entire lower end side of the inner surface 483a of the nozzle lid 483 is taken as the residual water occurrence portion S4 in FIGS. 9A and 9B, a part of the lower end side of the inner surface 483a of the nozzle lid 483 may be taken as the residual water occurrence portion.

The illuminator 600 can suppress the occurrence of bacteria and/or mold in the residual water occurrence portion S4 by irradiating the sterilizing light having an irradiation area S5 shown by the double dot-dash lines toward the residual water occurrence portion S4. In such a case, it is favorable for the maximum beam direction of the sterilizing light of the illuminator 600 to be directed toward the residual water occurrence portion S4.

For example, the illuminator 600 may include multiple residual water occurrence portions (e.g., the residual water occurrence portion S2 and the residual water occurrence portion S4) within the irradiation area of the sterilizing light. In such a case, for example, the occurrence of bacteria and/or mold inside the nozzle storage part 480 can be effectively suppressed by using experiments, simulations, etc., to direct the maximum beam direction of the sterilizing light toward a residual water occurrence portion at which the propagation of bacteria and/or mold is large and by setting the other residual water occurrence portions to be within the irradiation area of the sterilizing light.

Figure 10A:
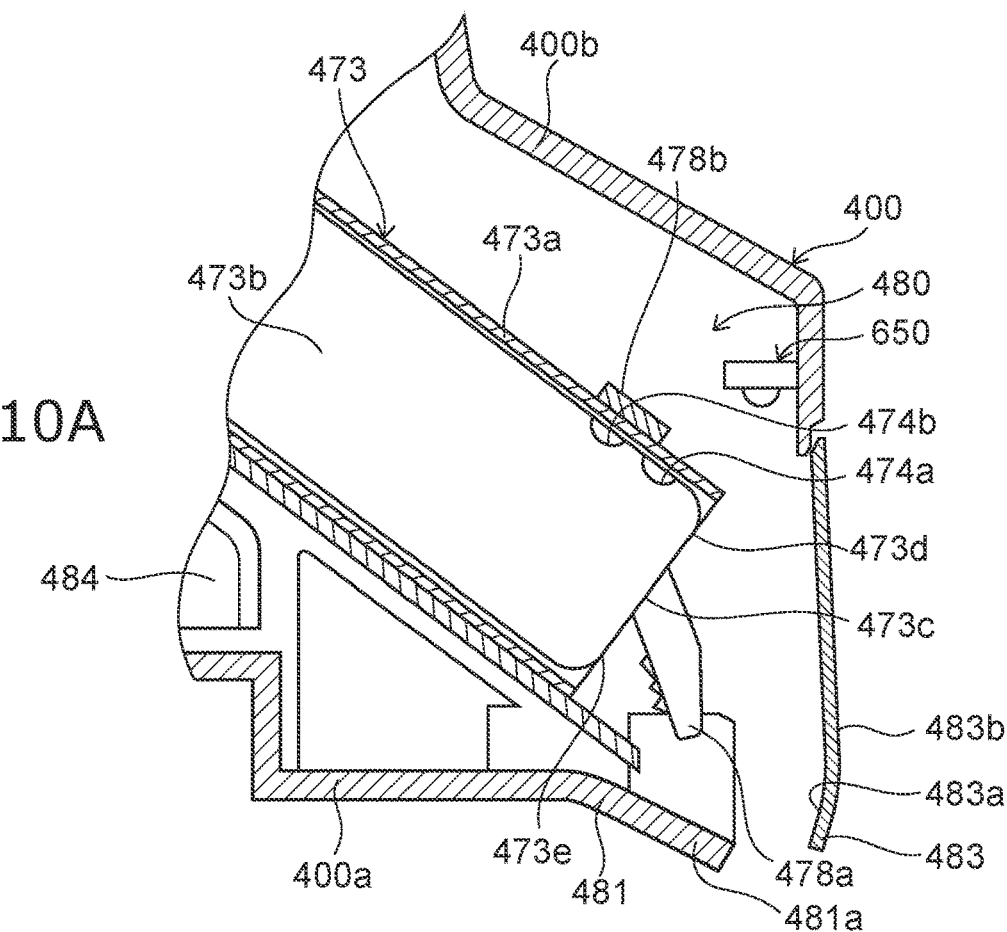
FIGS. 10A and 10B are explanatory drawings illustrating an illuminator according to a second modification that is provided above the nozzle.
Figure 10B:
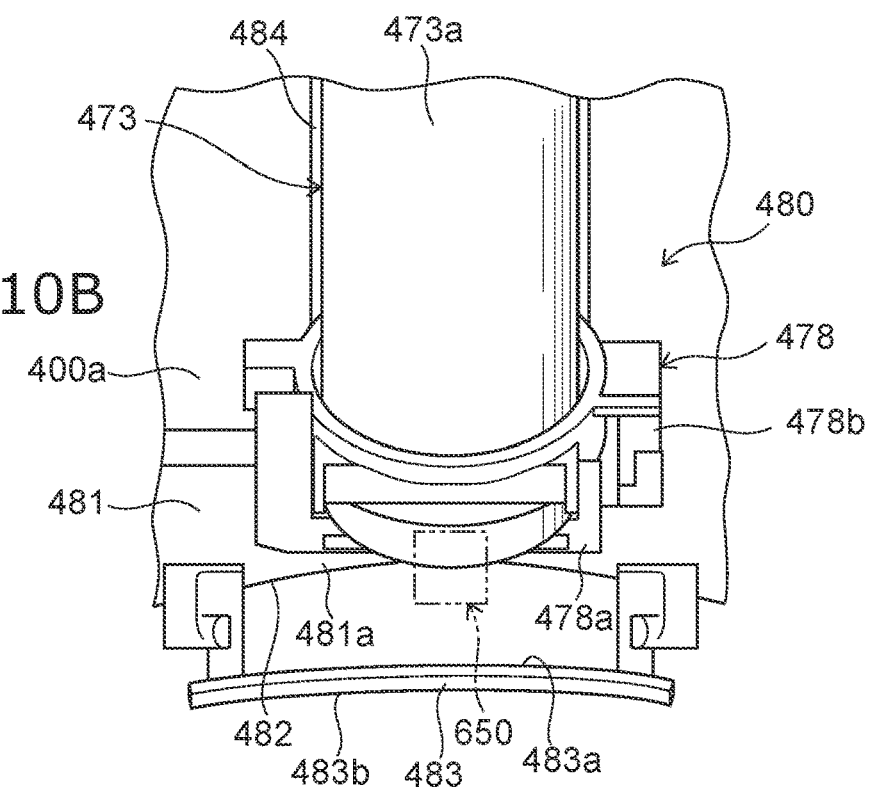

FIGS. 10A and 10B are explanatory drawings illustrating an illuminator according to a second modification that is provided above the nozzle. FIG. 10A is a cross-sectional view of the nozzle and the nozzle storage part when viewed from the side. FIG. 10B is a plan view of the nozzle and the nozzle storage part when viewed from above.

An example is described in the embodiment described above in which the illuminator 600 is located leftward of the nozzle storage part 480. However, the invention is not limited thereto; for example, as illustrated in FIGS. 10A and 10B, the illuminator 650 may be located above the nozzle 473. For example, the illuminator 650 can be provided at the case cover 400*b*. It is favorable for at least a part of the illuminator 650 to be located further frontward than the front surface 473*c* of the nozzle 473 in the state in which the nozzle 473 is retracted. Also, it is favorable for at least a part of the illuminator 650 to be located higher than the lower end 473*e* of the front surface 473*c* of the nozzle 473 in the state in which the nozzle 473 is retracted. Thereby, the sterilizing light can be efficiently irradiated toward the residual water occurrence portion.

Figure 11A:
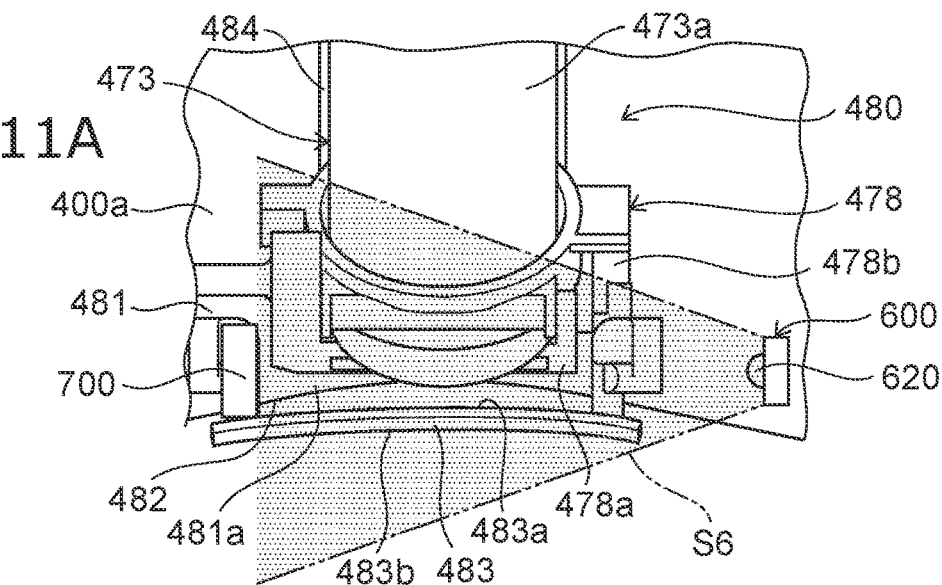
FIGS. 11A to 11C are explanatory drawings of an illuminator according to a third modification in which a reflective material that reflects the sterilizing light is provided at the opposite side in the lateral direction.
Figure 11B:
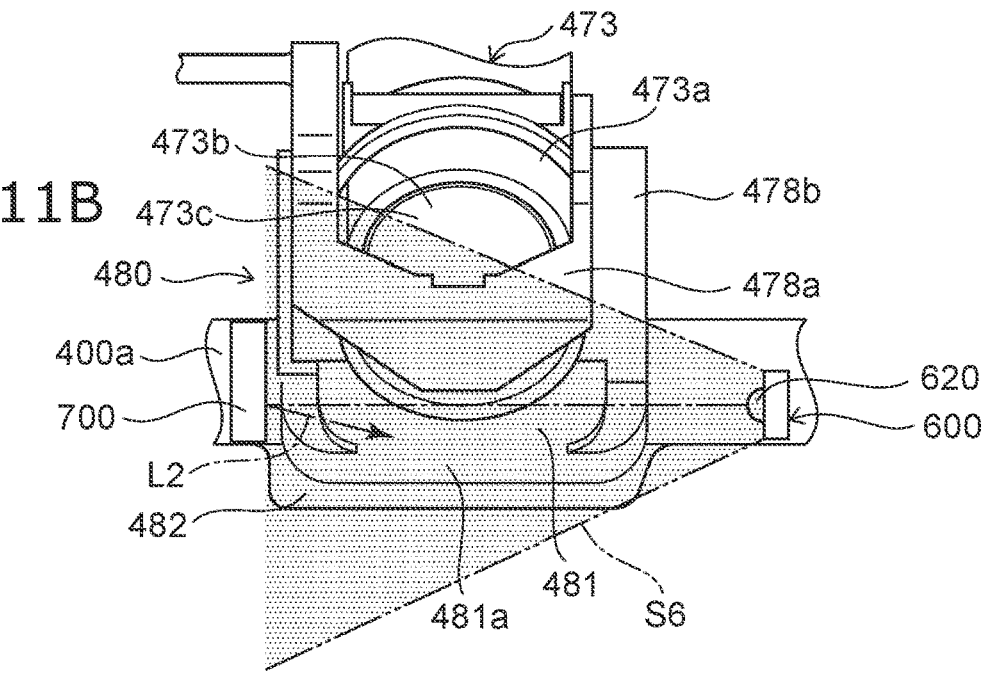
Figure 11C:
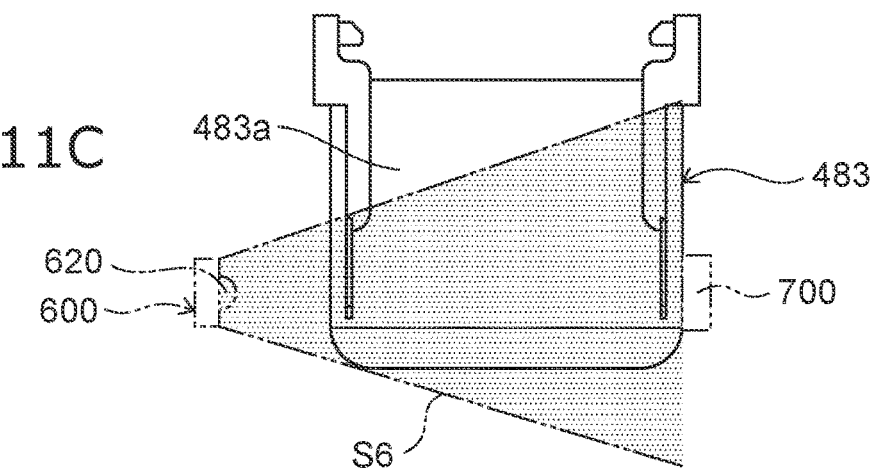

FIGS. 11A to 11C are explanatory drawings of an illuminator according to a third modification in which a reflective material that reflects the sterilizing light is provided at the opposite side in the lateral direction. FIG. 11A is a plan view of the nozzle and the nozzle storage part when viewed from above. FIG. 11B is a front view of the nozzle and the nozzle storage part when viewed from the front. The nozzle lid is not illustrated in FIG. 11B. FIG. 11C is a back view illustrating the inner surface side of the nozzle lid.

An example is described in the embodiment described above in which the sterilizing light is directly irradiated from the illuminator 600 toward the residual water occurrence portion S2. However, the invention is not limited thereto; for example, as in the third modification illustrated in FIGS. 11A to 11C, the nozzle storage part 480 may include a reflective material 700 that is positioned at the side opposite to the illuminator 600 in the lateral direction and reflects the sterilizing light toward the right side (the other side). Thereby, as shown by the double dot-dash lines in FIGS. 11A to 11C, an irradiation area S6 of the sterilizing light of the illuminator 600 can be wide, and the intensity of the sterilizing light on the residual water occurrence portion can be increased.

For example, the reflective material 700 is formed of a metal material to increase the reflectance. Also, it is desirable to perform mirror finishing of the surface of the reflective material 700 (the surface facing the illuminator 600). The reflective material 700 may be formed of a resin material having a high reflectance. For example, a fluoric compound or a polyester compound is used as such a resin material. The entire reflective material 700 may include a material having a high reflectance such as that described above, or only a part of the reflective material 700 may include a material having a high reflectance. For the reflective material 700 that is formed of such a material, it is favorable for the reflectance to be not less than 10%, and more favorably 50%. More favorably, the occurrence of bacteria and/or mold inside the nozzle storage part 480 can be effectively suppressed by using a reflective material 700 having a reflectance not less than 80%.

The illuminator 600 may irradiate the sterilizing light on the residual water occurrence portion S2 by using the reflective material 700 to reflect the sterilizing light. The sterilizing effect can be improved thereby because the sterilizing light can be doubly irradiated on the residual water occurrence portion S2. In other words, there is a risk that the intensity of the sterilizing light may be weak in the residual water occurrence portion S2 at positions separated from the illuminator 600. However, as illustrated by an optical axis L2 of FIG. 11B, the occurrence of bacteria and/or mold can be suppressed because the sterilizing light can be doubly irradiated on positions separated from the illuminator 600 by using the reflective material 700. Also, by adjusting the angle of the reflected light, the sterilizing light can be irradiated on residual water occurrence portions on which the illuminator 600 cannot directly irradiate. Accordingly, the interior of the nozzle storage part 480 can be effectively sterilized, and the occurrence of bacteria and/or mold can be suppressed.

Figure 12A:
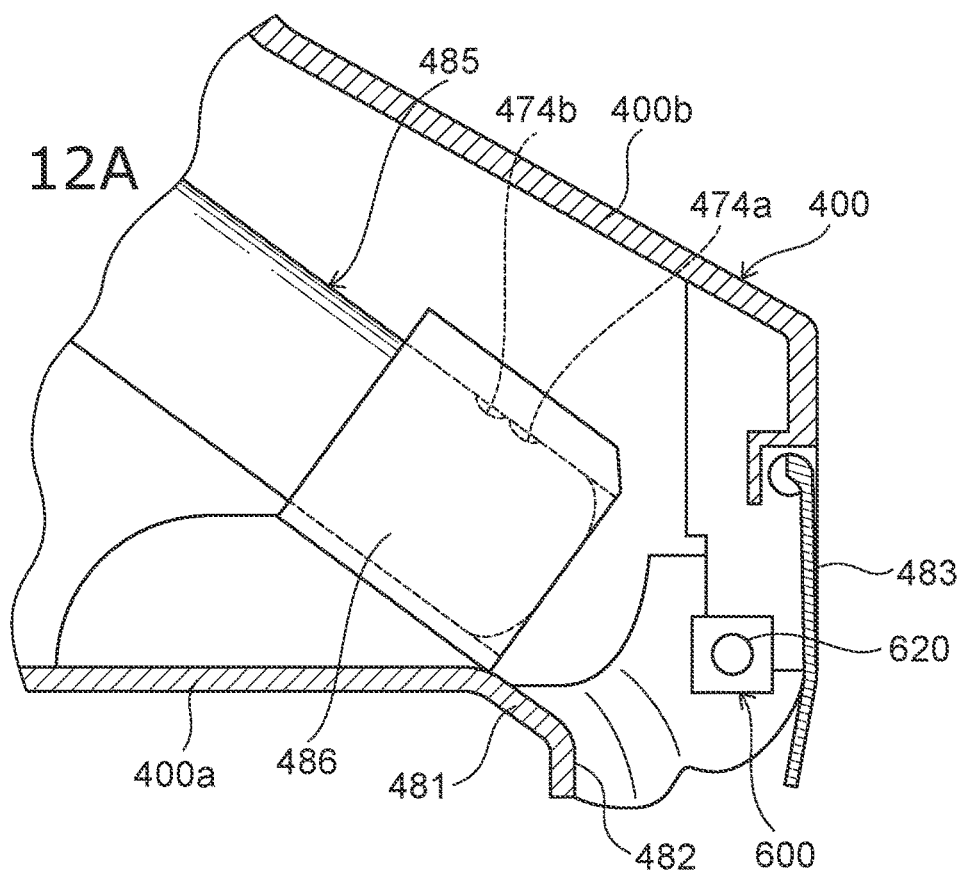
FIGS. 12A and 12B are cross-sectional views showing a private part washing nozzle according to a fourth modification.
Figure 12B:
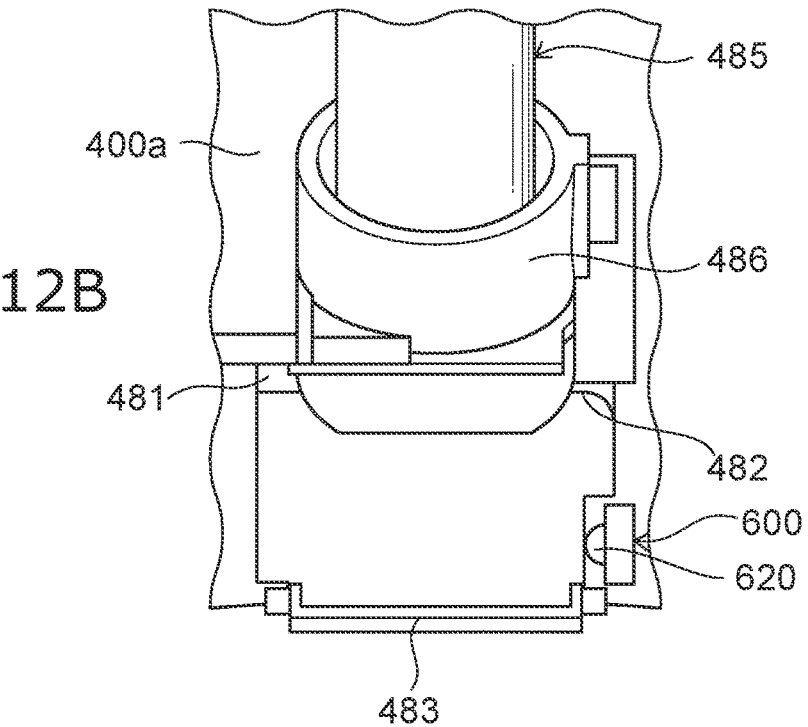

FIGS. 12A and 12B are cross-sectional views showing a private part washing nozzle according to a fourth modification. FIG. 12A is a cross-sectional view of the nozzle and the nozzle storage part when viewed from the side. FIG. 12B is a plan view of the nozzle and the nozzle storage part when viewed from above.

An example is described in the embodiment described above in which the nozzle 473 is a two-stage nozzle that extends and retracts in two stages. However, the invention is not limited thereto; for example, as in the fourth modification illustrated in FIGS. 12A and 12B, a nozzle 485 may be one nozzle that advances into the toilet 800 and then retracts. In such a case, a tubular nozzle washer 486 is provided to be at the tip side of the nozzle 485 when the nozzle 485 is retracted inside the casing 400. A water discharger that discharges sterilizing water and water toward the outer circumferential surface of the nozzle 485 is formed in the nozzle washer 486.

For example, the following aspects may be considered as sanitary washing devices based on the embodiments described above.

A first aspect includes a private part washing nozzle discharging water toward a private part of a user in a state of the private part washing nozzle being advanced into a toilet, a casing including a nozzle storage part configured to store an entirety of the private part washing nozzle in a state of the private part washing nozzle being retracted, a sterilizing water generator generating sterilizing water supplied to the private part washing nozzle and the nozzle storage part, and an illuminator irradiating sterilizing light into the nozzle storage part, such that the sterilizing light has a sterilizing action, and the illuminator irradiates the sterilizing light toward a residual water occurrence portion at which the sterilizing water supplied into the nozzle storage part remains.

According to the first aspect, the private part washing nozzle and the nozzle storage part can be washed and sterilized by the sterilizing water. In other words, a wide area of the private part washing nozzle and the nozzle storage part can be sterilized by the sterilizing water. The illuminator sterilizes the residual water occurrence portion at which the sterilizing water remains inside the nozzle storage part by irradiating the sterilizing light toward the residual water occurrence portion. In other words, the illuminator irradiates the sterilizing light toward the residual water occurrence portion at which bacteria and/or mold easily occur. Accordingly, even without providing multiple light sources, reflective materials, etc., the clean state of the private part washing nozzle and the nozzle storage part can be efficiently maintained using the sterilizing water and the sterilizing light, and the enlargement of the casing can be suppressed.

A second aspect is the first aspect, wherein the sterilizing water generator supplies the sterilizing water toward a water discharge port of the private part washing nozzle.

According to the second aspect, the sterilizing water sterilizes the bidet wash water discharge port and/or the bottom wash water discharge port of the private part washing nozzle and flows in the nozzle storage part. On the other hand, the illuminator irradiates the sterilizing light on the residual water occurrence portion of the sterilizing water flowing in the nozzle storage part from the private part washing nozzle. Accordingly, the private part washing nozzle and the nozzle storage part can be effectively sterilized by the sterilizing water and the sterilizing light.

A third aspect is the first or second aspect that further includes a water discharger discharging the sterilizing water toward the private part washing nozzle, and the sterilizing water generator supplies the sterilizing water toward the water discharger.

According to the third aspect, the sterilizing water sterilizes the outer circumferential surface (the central body) of the private part washing nozzle and flows in the nozzle storage part. On the other hand, the illuminator irradiates the sterilizing light on the residual water occurrence portion of the sterilizing water flowing in the nozzle storage part from the private part washing nozzle. Accordingly, the private part washing nozzle and the nozzle storage part can be effectively sterilized by the sterilizing water and the sterilizing light.

A fourth aspect is one of the first to third aspects, wherein the residual water occurrence portion includes a front end side of a bottom portion of the nozzle storage part.

According to the fourth aspect, the occurrence of bacteria and/or mold inside the nozzle storage part can be suppressed by irradiating the sterilizing light on the front end side of the bottom portion of the nozzle storage part at which the residual water of the sterilizing water easily occurs.

A fifth aspect is one of the first to fourth aspects, wherein the nozzle storage part includes a nozzle lid configured to open and close an opening provided in a front end of the nozzle storage part, and the residual water occurrence portion includes a lower end side of an inner surface of the nozzle lid.

According to the fifth aspect, the occurrence of bacteria and/or mold inside the nozzle storage part can be suppressed by irradiating the sterilizing light on the lower end side of the inner surface of the nozzle lid at which the residual water of the sterilizing water easily occurs.

A sixth aspect is one of the first to fifth aspects, wherein at least a part of the illuminator is located further frontward than the front surface of the private part washing nozzle in a state of the private part washing nozzle being retracted.

According to the sixth aspect, the surface area of a shadow caused by the private part washing nozzle obstructing the sterilizing light irradiated from the illuminator can be reduced. Also, because the illuminator is located proximate to the residual water occurrence portion for the residual water occurrence portions of the second and third aspects, the intensity of the sterilizing light irradiated on the residual water occurrence portion can be increased, and the occurrence of bacteria and/or mold of the residual water occurrence portion can be suppressed.

A seventh aspect is the one of the first to sixth aspects, wherein at least a part of the illuminator is located lower than a center of a front surface of the private part washing nozzle in a state of the private part washing nozzle being retracted.

According to the seventh aspect, the surface area of a shadow caused by the private part washing nozzle obstructing the sterilizing light irradiated from the illuminator can be reduced. Also, because the illuminator is located proximate to the residual water occurrence portion for the residual water occurrence portions of second and third aspects, the intensity of the sterilizing light irradiated on the residual water occurrence portion can be increased, and the occurrence of bacteria and/or mold of the residual water occurrence portion can be suppressed.

An eighth aspect is the seventh aspect, wherein at least a part of the illuminator is located higher than a lower end of a front surface of the private part washing nozzle in a state of the private part washing nozzle being retracted.

According to the eighth aspect, the residual water occurrence portion can be effectively located within the irradiation area because the irradiation area of the sterilizing light irradiated from the illuminator can be increased. Also, the enlargement of the casing can be suppressed because the illuminator does not protrude below the casing.

A ninth aspect is one of the first to eighth aspects, wherein the illuminator is located at one lateral-direction side of the nozzle storage part and irradiates the sterilizing light toward another lateral-direction side.

According to the ninth aspect, the illuminator can efficiently irradiate the sterilizing light toward the residual water occurrence portion extending in the lateral direction of the nozzle storage part.

A tenth aspect is the ninth aspect, wherein the nozzle storage part includes a reflective material on the other lateral-direction side, the reflective material reflecting sterilizing light, and the illuminator irradiates sterilizing light on the residual water occurrence portion by causing the sterilizing light to be reflected by the reflective material.

According to the tenth aspect, the sterilizing effect can be improved because the sterilizing light can be doubly irradiated on the residual water occurrence portion. Also, by adjusting the angle of the reflected light, the sterilizing light can be irradiated on residual water occurrence portions on which the illuminator cannot directly irradiate. Accordingly, the interior of the nozzle storage part can be effectively sterilized, and the occurrence of bacteria and/or mold can be suppressed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. For example, the shape, the dimension, the material, the disposition, the installation feature or the like of the components included in the sanitary washing device 100 are not limited to the illustration and can be appropriately modified. The components included in the embodiments described above can be combined within the extent of technical feasibility, and any combined components also are included in the scope of the invention to the extent that the feature of the invention is included.

What is claimed is:

1. A sanitary washing device, comprising:
a private part washing nozzle discharging water toward a private part of a user in a state of the private part washing nozzle being advanced into a toilet;
a casing including a nozzle storage part configured to store an entirety of the private part washing nozzle in a state of the private part washing nozzle being retracted;
a sterilizing water generator generating sterilizing water supplied to the private part washing nozzle and the nozzle storage part; and
an illuminator irradiating sterilizing light into the nozzle storage part,
the sterilizing light having a sterilizing action,
the illuminator irradiating the sterilizing light toward a residual water occurrence portion at which the sterilizing water supplied into the nozzle storage part remains.

2. The device according to claim 1, wherein
the sterilizing water generator supplies the sterilizing water toward a water discharge port of the private part washing nozzle.

3. The device according to claim 1, further comprising:
a water discharger discharging the sterilizing water toward the private part washing nozzle,
the sterilizing water generator supplying the sterilizing water toward the water discharger.

4. The device according to claim 1, wherein
the residual water occurrence portion includes a front end side of a bottom portion of the nozzle storage part.

5. The device according to claim 1, wherein
the nozzle storage part includes a nozzle lid configured to open and close an opening provided in a front end of the nozzle storage part, and
the residual water occurrence portion includes a lower end side of an inner surface of the nozzle lid.

6. The device according to claim 1, wherein
at least a part of the illuminator is located further frontward than a front surface of the private part washing nozzle in the state of the private part washing nozzle being retracted.

7. The device according to claim 1, wherein
at least a part of the illuminator is located lower than a center of a front surface of the private part washing nozzle in the state of the private part washing nozzle being retracted.

8. The device according to claim 7, wherein
at least a part of the illuminator is located higher than a lower end of a front surface of the private part washing nozzle in the state of the private part washing nozzle being retracted.

9. The device according to claim 1, wherein
the illuminator is located at one lateral-direction side of the nozzle storage part and irradiates sterilizing light toward an other lateral-direction side of the nozzle storage part.

10. The device according to claim 9, wherein
the nozzle storage part includes a reflective material on the other lateral-direction side, the reflective material reflecting sterilizing light, and
the illuminator irradiates sterilizing light on the residual water occurrence portion by causing the sterilizing light to be reflected by the reflective material.

* * * * *